United States Patent [19]

Pageat

[11] Patent Number: 5,709,863
[45] Date of Patent: Jan. 20, 1998

[54] PROPERTIES OF CATS' FACIAL PHEROMONES

[76] Inventor: Patrick Pageat, Lo Paniere - Route de Saint-Saturnin, R4400 Apt, France

[21] Appl. No.: 511,601

[22] Filed: Aug. 4, 1995

[30] Foreign Application Priority Data

Feb. 3, 1995 [EP] European Pat. Off. ............ 95400229

[51] Int. Cl.$^6$ ............ A61K 35/78; A61K 31/20
[52] U.S. Cl. ............ 424/195.1; 514/558
[58] Field of Search ............ 424/195.1; 514/558

[56] References Cited

U.S. PATENT DOCUMENTS 5,073,545  12/1991  Arima et al. ............ 514/27

*Primary Examiner*—John W. Rollins
*Attorney, Agent, or Firm*—Young & Thompson

[57] ABSTRACT

A composition containing an emulsion comprising a mixture of fatty acids or derivatives thereof and a compound of vegetal origin that has an attractive effect on cats. This composition can be utilized in a process for preventing cats from urinating a marked spot or to prevent anxiety in cats or to familiarize cats placed in a new environment.

20 Claims, 2 Drawing Sheets

Boosting effect on exploratory and feeding behaviors in an unknown place.

— Neutral reference lot (RL):

tE=270mn
       tF=312mn

— Reference lot with pheromone (RL-Ph)

tE=31mn
       tF=84mn

— Test lot (TL):

PROPERTIES OF CATS' FACIAL PHEROMONES

FIELD OF THE INVENTION

The present invention relates to a composition containing an emulsion comprising a mixture of fatty acids or derivatives thereof and a compound of vegetal origin that has an attractive effect on cats. This composition can be utilized in a process for preventing cats from urinating a marked spot or to prevent anxiety in cats or to familiarize cats placed in a new environment.

BACKGROUND AND PRIOR ART

Cats are often presented as forming a territory species, i.e., strongly bounded by a delimited surrounding which they organize in connection with their various behavioral functions. Indeed, their territory is not made up of just one area whose limits are set by odorous marks; it consists of an array of functional land patches linked to one another by passage tracks. The passage tracks never vary and they are gradually pioneered as the animals busy themselves exploring.

This complex system conforms to Waser and Wiley's definition of territorial grounds. Each territorial ground is used in conformity with a precise behavioral function, such as predatory hunting, game playing, interplay with congenerics or with other species.

In addition to their activity areas, cats also delineate one or more so-called isolation fields within which they seek safety whenever they wish to sleep or when they feel physically handicapped.

These complex systems can only be made workable through resorting to marks, whose odor beacons stabilize the whole structure.

Cats master several marking processes, materializing sometimes into visual stimuli (scratches, urine spots) but always into olfactive stimuli. These can be divided into the following three functional groups:

Group 1: The stricto Sensu Territorial Marks

Scratches and urine spurts from Group 1 are meant to express that some one is a sitting tenant of the place;

Group 2: The Alarm Marks

Marks from Group 2 are notably produced by the paw pad sweat glands or anal glands and entail the shunning of the so-delineated zone.

Group 3: The Identification or Familiar Growing Marks

Marks from Group 3 are produced by the face skin and are laid on any living or inert support that has been safely explored by the animal.

Although all these markings processes have a definite purpose, the markings produced by the facial secretions of cats have been quite controversial.

For instance, in 1979, Riegen and Walz Koenig (1979) in "Markieren Katzen beim Wagen reiben?", *Sauge tierk*, 44, pp 319–320, demonstrated that the facial sebaceous glands of cats are quite small and connected to hair follicles, which physiologically would not be associated with pheromonal production in these glands. Moreover, Rieger et al supra demonstrated that the brushing behavior by cats of objects is instigated by cats since the objects are usually odoriferous and hence the cats would impregnate themselves with this odor. However, the results of Rieger et al supra are disputable and have been highly contested.

However, the work published by Verberne and DeBoor (1976) "Chemo Communication among Domestic Cats", *Z. Tierpsychol.*, 42 pp. 86–109 and Verberne G. and Leyhaesen P. (1976) "Marking behavior of some Viverridae and Felidae: time-interval analysis of the marking pattern", *Behaviour*, 58, pp. 192–253, concluded that facial secretions combined with urinary pheromones inform the male cats of the female cats sexual receptiveness. These same authors indicated that this marking behaviour is shared by both male and female cats and that its frequency varies according to the individual animals. The facial marking appears to be less frequently set off by these pheromones than by urinary secretion. These authors also demonstrated that this type of facial marking could have a function of visual communication, since cats seem to facially work when approached by a known and accepted individual.

Finally, Verberne and De Boer supra renounced the hypothesis that saliva would be a pheromonal vector since facial marking is most of the time conducted when the cat's mouth is closed.

It is however well known that once a cat has sniffed and explored a support, it usually brushes one side of its face on the object, beginning with the chin, then sliding up to the lip corner and on to the hair-poor zone before the ear. This brushing is often interpreted as a show of affection; it is, in fact, an action in marking with secretions. These markings have until recently only been the object of strictly ethological approaches aiming at measuring their functional values.

Indeed, it is now known that cats possess facial pheromones and when they brush up against persons or objects with their face, they are actually leaving these secreted facial pheromones as a "mark". The facial marking properties of cats may be summed up under three headings, as follows:

a) Space spotting function

These marks are indeed mainly laid on objects placed at junction spots between a passage track and a territory patch. They are also spotted on other objects distinguished for their mass or their structure inside the field of activity. These marks seem to be instrumental in easing the cat's orientation.

b) Emotional stabilizing function

Let into an enclosure still unknown to it, and furnished with a rich variety of objects, the cat tends either to coil up in a corner, or to emit spurts of urine, as a way of marking which is heavily loaded with emotional charge (Dehasse 1990).

c) Relational function

Cats that share large portions of their territories with congenerics brush themselves against the latter. This action seems to amount to a genuine reciprocal marking that leads to creating a "herd odor".

Hence any intruder can be identified through its olfactory disharmony. Today, this phenomenon is used to ease the integration of a new cat into the family group.

In that instance, the pheromones must be spread on the new cat's face and flanks.

Today, the collecting and spreading of a cat's facial pheromones is a technique widely used by veterinarians to settle different conflicts between a cat and surrounding animals for an introduction tool.

However, the use of facial pheromones of cats is not limited only to settle conflicts between cats and surrounding animals. Indeed, it was recently discovered that the facial pheromones of cats can be utilized as a therapeutic tool for the treatment of reactive urinary markings. For instance, in "Utilisation des phéromones faciales du chat dans le traitement du marquage urinaire" ("Utilization of facial pheromones for the treatment of urinary markings in cats"), Premier Congrès FECAVA, Paris, November 1994 by Pageat, p. 1994, it was demonstrated that a functional antagonism between urinary secretions and facial excretions did indeed exist. Moreover, it was proven that an object marked by the cat's facial secretions will not be sprinkled with urine.

Furthermore, the facial pheromones of cats can also be utilized to familiarize cats placed in a new environment or to prevent anxiety in cats, after for example, surgical proceedings.

But collecting the natural pheromones is quite difficult and is often faultily handled, resulting in loss or contamination of the final product.

Thus it is an object of the present invention to overcome the problems associated with the prior art in obtaining facial pheromones from cats.

Another object of the present invention is a composition which is capable of preventing cats from urinating in a marked spot.

Yet another object of the present invention is to provide a novel composition for use in the cats surroundings that familiarizes cats to their new environment.

Yet another object of the present invention is to provide a composition that can be utilized to prevent anxiety in cats.

A composition that prevents urinary markings, familiarizes cats in a new environment and prevents anxiety in cats is also contemplated by the present invention.

This novel composition is also void of any toxicity to the cats and of any odor perceptible to man. It can be utilized effectively in a household environment.

These and other objects are achieved by the present invention as evidenced by the summary of the invention, description of the preferred embodiments and the claims.

SUMMARY OF THE PRESENT INVENTION

In one of the composition aspects, the present invention provides a composition comprising:
 (a) an emulsion comprising a mixture of fatty acids or derivatives thereof, said mixture being capable of preventing cats from urinating in a marked spot, and/or familiarizes cats in a new environment and/or prevents anxiety in cats; and
 (b) a compound of vegetal origin that has an attractive effect on cats.

Yet another composition aspect of the present invention is to provide a composition comprising from 5% to 32% (v %/v %) of:
 (a) an emulsion, said emulsion comprising diluted in an aqueous phase a mixture of fatty acids, said mixture comprising:
  (i) between about 62% (v %/v %) to about 86% (v %/v %) of oleic acid;
  (ii) between about 6% (v %/v %) to about 13% (v %/v %) of azelaic acid;
  (iii) between about 9% (v %/v %) to about 12% (v %/v %) of pimelic acid; and
  (iv) between about 13% (v %/v %) to about 24% (v %/v %) of palmitric acid; and
 (b) between about 2.5 ml/l to 8 ml/l of a composition of vegetal origin that has an attractive effect on cats.

Another aspect of the present invention provides a use of a novel composition to prevent urinary markings in cats.

Yet another use aspect of the present invention is to provide the present composition for use in treating a cat's anxiety.

In yet another use aspect, the present invention provides a composition for use in familiarizing cats that are placed in a new environment.

Thus, the present invention provides a composition in the form of an aqueous emulsion, spray and solution.

BRIEF DESCRIPTION OF THE DRAWINGS

FIG. 3 is a graphic representation of the effect on exploratory and feeding behaviors in an unknown place for cats. The test lot (TL) indicates that the cages were sprayed using the present invention before the cats were placed in these cages, RL-Ph were cages which had received pads impregnated with facial pheromones and (RL) were neutral cages with no added chemicals.

DETAILED DESCRIPTION OF THE PREFERRED EMBODIMENTS OF THE PRESENT INVENTION

Figure 1:
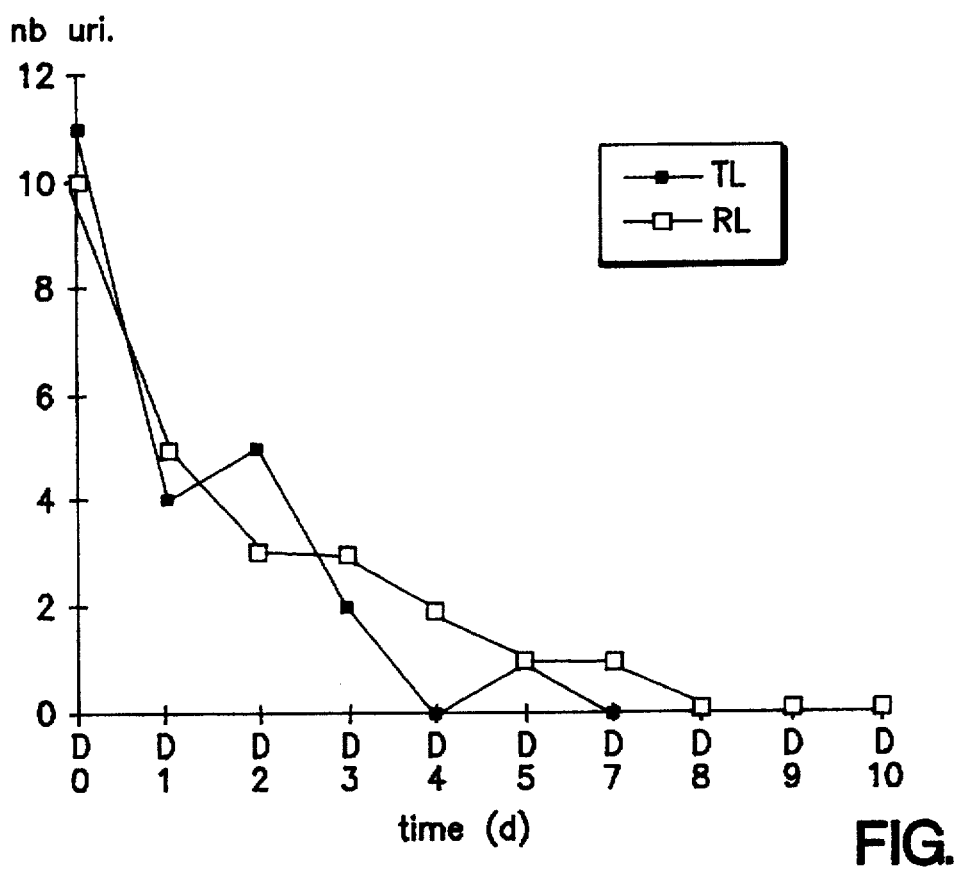
FIG. 1 is a graphic representation of a comparative test of cats receiving treatment of clomipraine 0.5 mg and the composition of the present invention (TL) and cats receiving clomipraine and pads impregnated with collected facial pheromones (RL).
Figure 2:
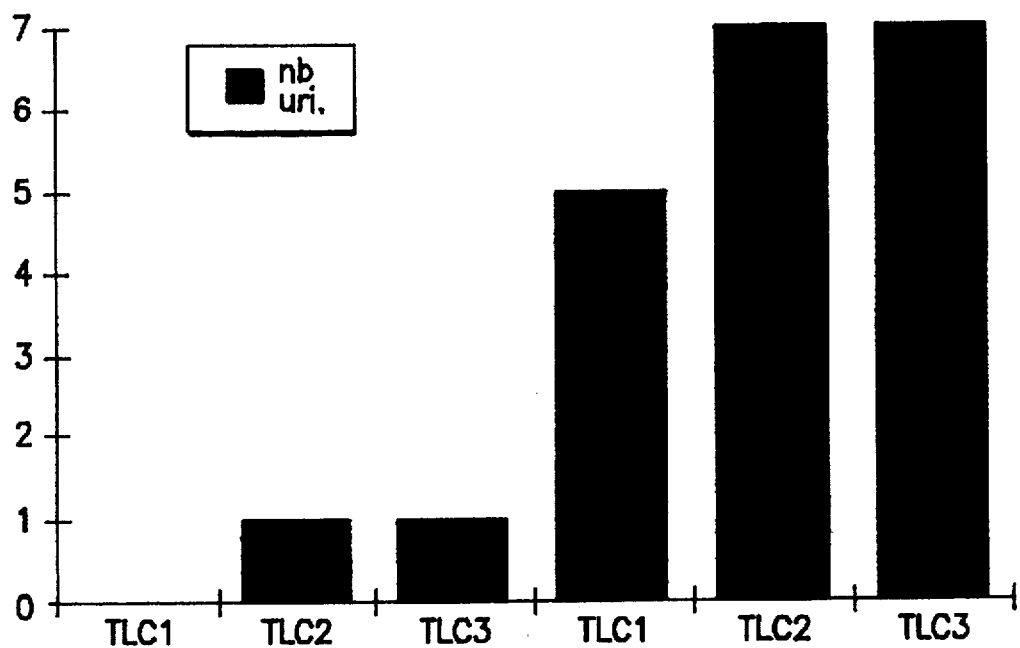
FIG. 2 is a graphic representation of a punctual inhibition test of a stud-rat and newly-laid urinary markings before using the composition of the present invention (RLC 1,2,3) and after using the composition of the present invention (TLC 1,2,3).

As used herein, the word "cat" encompasses any member of the family Felidae including the common domestic cat as well as the tiger, lion, leopard, mountain lion, lynx, bobcat, ocelot and the like.

By "pheromone" is meant a substance released by the body of a particular species that causes a predictable reaction by another individual of the same species, which substance may serve, for example, as a specific attractant, social communicator, sexual stimulant and the like.

By "urinary markings" is meant any fluid and dissolved substances excreted by the urinary system of a cat which, when excreted, identifies a known position and serves as a guide to this position.

As used herein "capable of preventing cats from urinating in a marked spot" means that cats will not urinate in a spot which they had previously urinated on.

By "emulsion" is meant a system containing at least two immiscible liquids in which one is dispersed in the form of very small globules, throughout the other.

By "attractive effect on cats" is meant that cats are attracted to this compound by scent.

By "familiarizing cats that are placed in a new environment" is meant the psycho-behaviour operation that appears after repeated positive or neutral contact with an object or a new individual. The familiarization operation combines behavioral procedures (exploration of an object, followed by its marking) and cognitive operations (memorization, association). According to the species, familiarization relies more on certain elements than on others. In Felidae, odoriferous marking is preponderant. The familiarized object or person will no longer set off fright or dread responses in the case of new contacts.

By the term "cat's anxiety" is meant that the cat has an apprehension of danger and dread accompanied by restlessness tension and the like, which is a reactional status characterized by a high probability to provide behavioral and emotional responses of fright. In neurophysical terms, this anxious state is accompanied by an hyperactivity of the noradrenergic and serotonin systems.

Indeed it was discovered that the compositions of the present invention have three effects on cats. These compositions prevent the cats from future urinary markings, or can familiarize cats in a new environment or prevent anxiety in cats. The compositions of the present invention can also be used in combination to prevent all three effects.

More specifically, the present invention is related to the identification of a composition that contains a synthetic hormone analogue and a compound of vegetal origin that has an attractive effect on cats.

It is well known within the art that pheromones from mammals are made up of volatile molecules, the essential components of these molecules being amines and fatty acids from indolic derivatives.

However, the facial pheromones of cats have never been thoroughly analyzed nor has their main chemical constituents been identified. Indeed, the only information ever published concerning cat's pheromones has been by Stoddart (1980), *The ecoloqy of vertebrate olfaction*, Chapman and Hall, London and New York, pp. 46–57.

To determine the acting pheromonal constituents of the facial secretions from cats, a preliminary study was first undertaken.

Since it is known that the pheromonal facial secretions do indeed vary with the sex, age, species and individual physiologic conditions, emotional conditions and hierarchical status of each cat, five different types of cats were chosen to standardize variances present in the cat's pheromones. For example, a sprayed Siamese she-cat, an entire male Persian cat, a castrated European he-cat, all having an age between 2 to 5 years old, as well as a 5-month old Birmese kitten and an eleven-year old sprayed European she-cat had their facial secretions analyzed.

All of the cats' faces were carefully swabbed for facial secretions. Sterile conditions are usually maintained during the swabbing procedure to prevent contamination from other chemical substances that may be present on the person conducting the swabbing or on the pads. Thus, the pads utilized are sterilized and the person conducting the swabbing wears sterilized surgical gloves. Any sterilized pads can be utilized which are known in the art. The period for swabbing may vary depending on the amount of substances one wants to remove. However, it is most preferable to swab the faces of cats during a 10-day period, preferably every two days during this period using 4 pads for each side of the cat's face. The pads are generally rubbed twice starting from the chin and going up to the corner of their lips and further to the area behind their ear. If these impregnated pads are not processed by HPLC immediately, they can be stored in thermosealed airtight bags at −18° C. until further processing.

After the swabs are taken, an analysis is conducted by HPLC to determine the chemical composition of the swabs. Each group of 4 pads, which correspond to a given date, is analyzed as a distinct swab, in order to increase the chances of observing variations. Thus, 10 swabs for each cat, i.e., a total of 50 analyzed swabs for 5 cats are then analyzed.

The swabs are first treated with an organic solvent. Any solvent can be utilized that is compatible to extract hydrophobic substances such as the fatty acids present on these swabs. It is preferable to use an organic solvent of methylic alcohol ($CH_3OH$)/$H_2O$ 65:35. After being subjected to the organic solvent, the samples are then run on an HPLC. Two columns can be used: a 4 μm C-18 and a 4 μm-CN, each having 15 cm×3.9 mm dimensions, the flow rate being 2 $cm^3mn^{-1}$ and having an UV detector at an absorption of 254 nm. The different fatty acids are eluted with a methylic acid:water (65:35) solvent.

Each fraction is then further analyzed to test for certain behavioral effects in cats. Thus F1, F2, F3, F4 and F5 were tested for prevention of cat's repeat urinal markings, familiarization of cats in a new environment and for cat's anxiety. Each fraction had effects in all and in combination for the above-mentioned behavior.

In a preferred embodiment, the composition of the present invention comprises oleic acid, cis-9-octaderenoic acid, azelaic acid, ($HOOC-(CH_2)_7-COOH$) (1,7-heptanedicarboxylic acid), pimelic acid ($HOOC-(CH_2)_5-COOH$) (heptanedioxyc acid), which is an intermediate formed in the oxidation of oleic acid and a precursor of biotin and palmitic acid (hexadecanoic acid), which is a saturated fatty acid occuring in palm oil and other fats. Derivatives of these fatty acids can also be utilized in the present invention. These derivatives can easily be tested for their efficacy to treat, for example, repetitive urinary markings and cat's anxiety according to the present invention.

The ranges of the above fatty acids may vary in this composition. The ranges of the specific fatty acids that may be utilized and certain percentages of these components in the composition may be ascertained and tested according to the methods of the present invention. It is preferable to use from about 62% to 86% (v %/v %) of oleic acid, from about 6% to about 13% (v %/v %) of azelaic acid; from about 9% to about 12% (v %/v %) of pimelic acid and about 13% to about 24% (v %/v %) of palmitic acid. It is most preferable to use about 68% oleic acid, 8% of azelaic acid, 9% pimelic acid and 15% palmitic acid.

All of these fatty acids are freely available from, for example, SIGMA® Chemical Company.

The above-described percentages of fatty acids are then mixed and diluted in distilled water to form an emulsion. An emulsion stabilizer such as glycerine may also be added, as known in the art. A quantity of ethanol (65°–90° GL) may also be added to this emulsion to enhance the formulation of the final product. The concentration of the combined fatty acids may vary in this dilution from 5% (v %/v %) total fatty acid components: 95% distilled water to 32% (v %/v %) total fatty acid components to 68% distilled water. It is preferable to use about 8% of the total fatty acid components to 92% water.

Once the fatty acid components are diluted appropriately to form the synthetic pheromonal analogue, a substance of vegetal origin is then added not only to bind the extremely fatty acid components, but also to maintain the attraction to cats of this synthetic pheromonal analogues at greater distances, to prevent the delay in the location of the product. Substances which act as conveyance molecules include but are not limited to extracts of Valeriana, subspecies of Valeriana such as *Valeriana Officinalis L.* (Codex Valeriana tint) and the like. Modifications of the vegetal components are also encompassed by the present invention, so long as their attraction ability is not effected.

In a similar manner, other synthetic formulations of fractions F1, F2, F4 and F5 can be achieved as that described above for fraction F3. Different combinations of these fractions to treat the various behavioral effects are also contemplated and within the person's skilled in the art to formulate using the compounds disclosed in the present invention.

The composition of the present invention can be formulated in any form such as a powder, spray, liquid or aerosol having components known to those skilled in the art. For example, for an optimal dose, 5 ml/liter of *Valeriana Officinalis L.* per 8% of the fatty acid emulsion can be placed in a spray container or lyophilized as a powder or placed in an aerosol can, with the appropriate propellants. The liquid, spray or powder can be applied to areas of the house in which the cat has urinated to prevent future urination at the same place. The composition of the present invention can also be utilized for use in cages to promote familiarization of cats when being housed in a foreign surrounding. The composition of the present invention is quite beneficial for cats that have undergone surgery to prevent anxiety promoting a quicker recovery for the cat.

In order to further illustrate the present invention and advantages thereof, the following specific examples are given, it being understood that the same are intended only as illustrative and in nowise limitative.

EXAMPLE 1

Isolation and Analysis of Components in Facial Secretions of cats

A sprayed Siamese she-cat, an entire male Persian cat and a castrated European he-cat of ages between 2 to 5 years old, as well as a 5-month old Birmese kitten and an 11-year old sprayed female cat were utilized in this example.

Swabs were made under sterile conditions using sterilized compresses on each cat every 2 days during a 10-day period, on the basis of 4 pads for each side of the face. The pads were rubbed twice starting from the chin of the cat and going up to the corner of their lips and further to the area before the ear.

Each group of 4 pads, which corresponded to a given date, was analyzed via HPLC as a distinct swab, in order to increase the chances of observing variations. Thus, 10 swabs for each cat, i.e., a total of 50 swabs were analyzed for the 5 cats.

The swabs were first treated with an organic solvent, methylic alcohol $(CH_3OH)/H_2O$ 65:35. Two HPLC columns were used: a 4 μm C-18 and a 4 μm-CN, both of them being 15 cm×3,9 mm in dimension. The column flow was set at 2 $cm^3$ $mn^{-1}$ and the absorption was set at 254 nm (UV). The different fatty acids are eluted with a methylic acid:water (65:35) solvent.

After analyzing the peaks obtained by HPLC, a group of 13 chemical compounds shared by all the tested cats was prevalent. The extreme concentration values obtained in all samples were retained to set the following value ranges:

oleic acid: 43%–65%
palmitic acid: 7%–26%
propionic acid: 4%–32%
azelaic acid: 3%–18%
pimelic acid: 8%–22%
5-aminovaleric acid: 5%–11%
iso-butyric acid: 9%–14%
n-butyric acid: 3%–17%
α-methylbutyric acid: 2%–9%
caproic acid: 5%–11%
p-hydroxyphenylacetic acid: 6%–19%
5β-cholestan acid 3β-ol: 2%–16%
trimethylamine: 3%–7%

After analysis of the quantitative variations of these various substances, the existence of functional subgroups within these substances, which vary in a "synchronic" way, was noted. It was logically deduced that this binding between the fluctuations represented a functional binding between these compounds. This was indeed supported by the numerous effects of the natural pheromone.

Five functional subgroups or fractions were then defined, which will be referred to as F1, F2, F3, F4, F5. These functional groups contain the following compounds:

F1
oleic acid: 34%–41%
caproic acid: 18%–32%
trimethylamine: 3%–5%
5-aminovaleric acid: 6%–9%
n-butyric acid: 5%–15%
α-methylbutyric acid: 6%–9%

F2
oleic acid: 38%–62%
palmitic acid: 17%–49%
propionic acid: 11%–23%
p-hydroxyphenylacetic acid: 6%–15%

F3
oleic acid: 62%–86%
azelaic acid: 6%–13%
pimelic acid: 9%–12%
palmitic acid: 13%–24%

F4
5β-cholestan acid 3β-ol: 13%–27%
oleic acid: 33%–39%
pimelic acid: 11%–24%
n-butyric acid: 14%–30%

F5
palmitic acid: 28%–37%
isobutyric acid: 11%–18%
5-aminovaleric acid: 9%–15%
n-butyric acid: 2%–12%
α-methylbutyric acid: 5%–8%
trimethylamine: 2%–6%
azelaic acid: 7%–17%
p-hydroxyphenylacetic acid: 8%–19%

EXAMPLE 2

Formulation of Chemical Composition of Fraction 3

A 68% oleic acid, 8% azealic acid, 9% primelic acid and 15% palmitic acid were mixed and then diluted in 1 liter distilled water or saline to form an emulsion having a concentration of about 8% fatty acids. To this emulsion was added 5 ml/l of *Valeriana Officinalis L.* The solution was then stirred until an aqueous solution was produced.

EXAMPLES 3 to 6

In a similar manner, as in Example 2, the following formulations are made:

EXAMPLE 3 oleic acid: 38%
caproic acid: 28% trimethylamine: 4%
5-aminovaleric acid: 5%
n-butyric acid: 9%
α-methylbutyric acid: 15%

EXAMPLE 4 oleic acid: 50%
palmitic acid: 30%
propionic acid: 11%
p-hydroxyphenylacetic acid: 9%

EXAMPLE 5

5β-cholestan acid 3β-ol: 20%
oleic acid: 35%
pimelic acid: 20%
n-butyric acid: 25%

EXAMPLE 6 palmitic acid: 35%
isobutyric acid: 11%
5-aminovaleric acid: 9%
n-butyric acid:3%
α-methylbutyric acid: 6%
trimethylamine: 6%
azelaic acid: 16%
p-hydroxyphenylacetic acid: 14%

EXAMPLE 7

Inhibition Potential of Urinary Marking

A first test was conducted on 22 cats that were brought to the consulting-room because of uncleanness. They were chosen since their case was tied to reactive urinary marking. These animals had not been medically treated in any way during the 21-day span that preceded their admission in the experiment.

After their physiological and behavioral conditions had been clinically examined, they were put down on a random sampling-list which provided treatment in a non-systematic way.

The test lot (TL) received a treatment associating clomipramine (0.5 mg/kg a day in two takes) and the composition of Example 2.

The reference lot (RL) was given clomipramine and the cat's owners had to apply pads impregnated with collected facial pheromones on their cats.

The follow-up was carried out daily by phone from day 0 to day 10. Each checking led to the entry of the exact number of laid markings.

The entered results were gathered in FIG. 1 which showed for each checking the average number of markings in each lot. The evaluation of reduced-margin RM does not show any significant difference between the two lots, at the 1% threshold.

EXAMPLE 8

Punctual Inhibition Test of a Newly-laid Urinary Marking from a Stud-cat

Three stud-cats with abundant marking power were used in this study. A cardboard block, 6 inches high, was placed in a treatment cage. A she-cat in heat was locked in another cage close by.

A stud-cat was let into the first cage. As soon as he had spurted his marking on the cardboard block, the cat was taken out of the cage, which was thoroughly cleaned with a disinfecting solution (Septisec®), except for the block.

The block was placed back into the cage and a second stud-cat was introduced who stayed in the cage for ten minutes.

It was noted whether or not he marked the block. This procedure was repeated, the block being changed after the second visitor (initial marker, then second marker).

The same experiment was then carried out six times as way of proof-checking.

A second procedure was initiated, but this time before introducing the second he-cat, the urinary marks staining the block were sprayed either with the composition of Example 2 or with the composition of Example 2 diluted in water.

The results were entered in FIG. 3. They set off the very strong efficiency of the composition of Example 2 since only two urinary markings were noted on the sprayed block in contrast with 9 to 14 markings in the other cases.

EXAMPLE 9

Boosting Effect on Exploratory and Feeding Behaviors in an Unknown Place

A population of 56 cats admitted for minor surgery and unaffected in their general health conditions were selected for this study. Following selection they were put down on a random choice list allowing to assign them a treatment in their cages.

The test lot (TL) was placed in a cage whose four corners, as well as the ground sheet, had beforehand been sprayed with the composition of Example 2.

The reference lot with pheromone (RL-Ph) was placed in another cage whose corners had received pads impregnated with facial pheromones, the ground-sheet being similarly impregnated.

The neutral reference lot (RL) made use of a neutral cage.

Each one of all these cages received a bowl, the innersides of which had been rubbed with kitten food. Notes were taken of the time spans elapsing before the caged cats started exploring (tE) and looking around for food (tF) and finally scenting and licking the bowl. The results collected in FIG. 3 showed quite a wide difference between lot WL and the other two lots.

Cats whose cage was sprayed resumed a normal behavior in a much quicker way.

No statistically significant difference lies between lots TL and RL-Ph(×2).

Therefore the composition of the present invention seemed to possess appeasing properties comparable with those observed with the natural pheromone.

EXAMPLES 10 to 13

The inhibition test in Examples 7 and 8 and the exploratory and feeding behavior in Example 9 are followed exactly, except that the composition of Example 2 is replaced by the compositions in Examples 3 to 6. Similar results are obtained for these tests.

EXAMPLE 14

Domestic Use

The composition of Example 2 is utilized in this example.

Previous urinary markings in a house is noted by the owners of the cat. These urine spots are noted on a chair and in general on other verticle pieces such as the table and dresser. The composition of Example 2 is applied to the areas wherein the cat urinated on the onset of noting the urine spots and repeat applications are performed once a day for 5 days.

No future urine markings are found in these areas after application of the composition in Example 2, no odors were noticeable during the utilization of this compound.

While the invention has been described in terms of various preferred embodiments, the skilled artisan will appreciate that various modifications, substitutions, omissions and changes may be made without departing from the scope thereof. Accordingly, it is intended that the scope of the present invention be limited solely by the scope of the following claims, including equivalents thereof.

I claim:

1. A composition comprising:
   (a) an emulsion comprising a mixture of oleic acid, azelaic acid, pimelic acid and palmitic acid, said mixture being capable of preventing cats from urinating in a marked spot; and
   (b) a compound of vegetal origin that has an attractive effect on cats.

2. The composition according to claim 1, wherein said mixture is present in a final concentration of between about 5% to 32% and comprises between about 62% (v %/v %) to about 86% (v %/v %) of oleic acid, between about 6% (v %/v %) to about 13% (v %/v %) of azelaic acid, between about 9% (v %/v %) to about 12% (v %/v %) of pimelic acid and between about 13% (v %/v %) to about 24% (v %/v %) of palmitic acid.

3. The composition according to claim 1, wherein said compound of vegetal origin is an extract of Valeriana.

4. The composition according to claim 1, wherein said compound of vegetal origin is an extract of *Valeriana officinalis*.

5. A composition comprising from 5% to 32% (v %/v %) of:
   (a) an emulsion, said emulsion comprising diluted in an aqueous phase a mixture of fatty acids, said mixture comprising:
      (i) between about 62% (v %/v %) to about 86% (v %/v %) of oleic acid;
      (ii) between about 6% (v %/v %) to about 13% (v %/v %) of azelaic acid;
      (iii) between about 9% (v %/v %) to about 12% (v %/v %) of pimelic acid; and
      (iv) between about 13% (v %/v %) to about 24% (v %/v %) of palmitric acid; and
   (b) between about 2.5 ml/l to 8 ml/l of a composition of vegetal origin that has an attractive effect on cats.

6. The composition according to claim 5, wherein said composition of vegetal origin is an extract of *Valeriana officinalis*.

7. The composition according to claim 5, wherein said mixture comprises about 68% oleic acid, about 8% azelaic acid, about 9% pimelic acid and about 15% palmitic acid.

8. The composition according to claim 5, where said mixture has a concentration of about 8%.

9. The composition according to claim 5, wherein said composition of vegetal origin has a concentration of about 5 ml/liter of emulsion containing said mixture.

10. A composition comprising:
    (a) an emulsion comprising a mixture of oleic acid, caproic acid, palmitic acid, azelaic acid, pimelic acid, 5-aminovaleric acid, n-butyric acid, α-methylbutyric acid, propionic acid, p-hydroxyphenylacetic acid, 5β-cholestane 3β-ol acid, and isobutyric acid and an amine, said mixture being capable of preventing cats from urinating in a marked spot, familiarizing cats in a new environment preventing anxiety in cats; and
    (b) a compound of vegetal origin that has an attractive effect on cats.

11. The composition according to claim 10, wherein said amine is trimethylamine.

12. The composition according to claim 10, wherein said compound of vegetal origin is an extract of Valeriana.

13. The composition according to claim 12, wherein said compound of vegetal origin is an extract of *Valeriana officinalis*.

14. A composition comprising from 5% to 32% (v %/v %) of:
    (a) an emulsion, said emulsion comprising diluted in an aqueous phase a mixture of fatty acids and an amine, said mixture comprising:
       (i) between about 34% (v %/v %) to about 41% (V %/V %) of oleic acid;
       (ii) between about 18% (v %/v %) to about 32% (v %/v %) of caproic acid;
       (iii) between about 3% (v %/v %) to about 5% (v %/v %) of trimethylamine;
       (iv) between about 6% (v %/v %) to about 9% (v %/v %) of 5-aminovaleric acid;
       (v) between about 5% (v %/v %) to about 15% (v %/v %) of n-butyric acid;
       (vi) between about 6% (v %/v %) to about 9% (v %/v %) of α-methylbutyric acid; and
    (b) between about 2.5 ml/l to 8 ml/l of a composition of vegetal origin that has an attractive effect on cats.

15. A composition comprising from 5% to 32% (v %/v %) of:
    (a) an emulsion, said emulsion comprising diluted in an aqueous phase a mixture of fatty acids, said mixture comprising:
       (i) between about 38% (v %/v %) to about 62% (V %/V %) of oleic acid;
       (ii) between about 17% (v %/v %) to about 49% (v %/v %) of palmitic acid;
       (iii) between about 11% (v %/v %) to about 23% (v %/v %) of propionic acid;
       (iv) between about 6% (v %/v %) to about 15% (v %/v %) of p-hydroxyphenylacetic acid; and
    (b) between about 2.5 ml/l to 8 ml/l of a composition of vegetal origin that has an attractive effect on cats.

16. A composition comprising from 5% to 32% (v %/v %) of:
    (a) an emulsion, said emulsion comprising diluted in an aqueous phase a mixture of fatty acids, said mixture comprising:
       (i) between about 13% (v %/v %) to about 27% (V %V %) of cholestane acid 3β-ol;
       (ii) between about 33% (v %/v %) to about 39% (v %/v %) of oleic acid;
       (iii) between about 11% (v %/v %) to about 24% (v %/v %) of pimelic acid;
       (iv) between about 14% (v %/v %) to about 30% (v %/v %) of n-butyric acid; and
    (b) between about 2.5 ml/l to 8 ml/l of a composition of vegetal origin that has an attractive effect on cats.

17. A composition comprising from 5% to 32% (v %/v %) of:
  (a) an emulsion, said emulsion comprising diluted in an aqueous phase a mixture of fatty acids and an amine, said mixture comprising:
    (i) between about 28% (v %/v %) to about 37% (V %/V %) of palmitic acid;
    (ii) between about 11% (v %/v %) to about 18% (v %/v %) of isobutyric acid;
    (iii) between about 9% (v %/v %) to about 15% (v %/v %) of 5-aminovaleric acid;
    (iv) between about 2% (v %/v %) to about 12% (v %/v %) of n-butyric acid;
    (v) between about 5% (v %/v %) to about 8% (v %/v %) of α-methylbutyric acid;
    (vi) between about 2% (v %/v %) to about 6% (v %/v %) of trimethylamine;
    (vii) between about 7% (v %/v %) to about 17% (v %/v %) of azelaic acid;
    (viii) between about 8% (v %/v %) to about 19% (v %/v %) of p-hydroxyphenylacetic acid; and
  (b) between about 2.5 ml/l to 8 ml/l of a composition of vegetal origin that has an attractive effect on cats.

18. A new method for preventing cats from urinating in a marked spot comprising the step of:
  i) placing or spraying in said marked spot a composition comprising:
    (a) an emulsion comprising a mixture of oleic acid, azelaic acid, pimelic acid and palmitic acid; and
    (b) a compound of vegetal origin that has an attractive effect on cats.

19. A method for treating a cat's anxiety comprising the step of:
  i) placing or spraying around the cat a composition comprising:
    (a) an emulsion comprising a mixture of oleic acid, azelaic acid, pimelic acid and palmitic acid and an amine; and
    (b) a compound of vegetal origin that has an attractive effect on cats.

20. A method for familiarizing cats in a new environment comprising the step of:
  i) spraying or placing around the cat a composition comprising:
    (a) an emulsion comprising a mixture of fatty acids oleic acid, caproic acid, palmitic acid, azelaic acid, pimelic acid, 5-aminovaleric acid, n-butyric acid, and an amine; and
    (b) a compound of vegetal origin that has an attractive effect on cats.

* * * * *

UNITED STATES PATENT AND TRADEMARK OFFICE
CERTIFICATE OF CORRECTION

PATENT NO. : 5,709,863
DATED : January 20, 1998
INVENTOR(S) : Patrick PAGEAT

It is certified that error appears in the above-indentified patent and that said Letters Patent is hereby corrected as shown below:

Column 12, line 59 (claim 16, line 7), change "cholestane acid 3β-ol;"

to --5β-cholestane acid 3β-ol;--.

Signed and Sealed this

Fourteenth Day of April, 1998

*Attest:*

BRUCE LEHMAN

*Attesting Officer*     *Commissioner of Patents and Trademarks*